United States Patent
Hoppe-Seyler et al.

(10) Patent No.: US 7,544,768 B2
(45) Date of Patent: Jun. 9, 2009

(54) PEPTIDES FOR INDUCING APOPTOSIS IN TUMOR CELLS

(75) Inventors: Karin Hoppe-Seyler, Hirschberg (DE); Felix Hoppe-Seyler, Heidelberg (DE); Irena Crnkovic-Mertens, Heidelberg (DE); Christian Rausch, Sandhausen (DE)

(73) Assignee: Deutsches Krebsforschungszentrum Stiflung des Offentlichen Rechts, Heidelberg (DE)

( * ) Notice: Subject to any disclaimer, the term of this patent is extended or adjusted under 35 U.S.C. 154(b) by 80 days.

(21) Appl. No.: 10/519,539

(22) PCT Filed: Jul. 1, 2003

(86) PCT No.: PCT/EP03/06958

§ 371 (c)(1), (2), (4) Date: Mar. 15, 2005

(87) PCT Pub. No.: WO2004/003008

PCT Pub. Date: Jan. 8, 2004

(65) Prior Publication Data

US 2005/0203288 A1 Sep. 15, 2005

(30) Foreign Application Priority Data

Jul. 1, 2002 (EP) .................................. 02014074

(51) Int. Cl.
*C07K 5/00* (2006.01)
*A61K 38/00* (2006.01)

(52) U.S. Cl. .......................................... 530/300; 514/2
(58) Field of Classification Search ................. 530/300; 514/2
See application file for complete search history.

(56) References Cited

U.S. PATENT DOCUMENTS

2007/0003535 A1 * 1/2007 Reed et al. ................. 424/94.2

FOREIGN PATENT DOCUMENTS

| WO | WO 02/16402 A2 | 2/2002 |
| WO | WO 02/26775 A2 | 4/2002 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Du et al (Cell, 2000, 102:33-42).*
Dermer (Bio/Technology, 1994, 12:320) t.*
Zips et al (2005, In Vivo, 19:1-7).*
Examination of Patent Applications Containing Nucleotide Sequences, p. 1-3.*
Franklin et al, Biochemistry, 2003, 42:8223-8231.*
Wang et al, Cancer Gene Therapy, 2008, 15:402-412.*

\* cited by examiner

*Primary Examiner*—Laura B Goddard
(74) *Attorney, Agent, or Firm*—Foley & Lardner LLP

(57) ABSTRACT

The present invention relates to peptides which interact with IAPs. IAPs are highly expressed in tumor cells which fail to undergo apoptosis. By binding to IAPs, the peptides of the present invention release tumor cells from the apoptosis block and thus provide a new tool for effective cancer therapy.

6 Claims, 4 Drawing Sheets

SEQUENCE LISTING

<160> NUMBER OF SEQ ID NOS: 132

<210> SEQ ID NO 1
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 1

Trp Leu Gly Thr Phe Ser Gly Thr Cys Ser Thr Ala Phe Tyr Phe Pro
1               5                   10                  15

Leu Gly Val Pro
            20

<210> SEQ ID NO 2
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 2

Cys Arg Trp Leu Arg Thr Lys Arg Thr Leu Pro Leu Phe Ser Val Met
1               5                   10                  15

Pro Phe Trp Cys

```
                            20

<210> SEQ ID NO 3
<211> LENGTH: 31
<212> TYPE: PRT
<213> ORGANISM: Artificial Sequence
<220> FEATURE:
<223> OTHER INFORMATION: randomized peptide that bind to particular IAPs

<400> SEQUENCE: 3

Met Tyr Ser Asn Val Ser Val Asp Val Ala Ala Asp Gly Val Ser Cys
1               5                   10                  15

Val Cys Cys Ser Trp Ser Val Gln Asn Asp Arg Pro Asp Ser Gly
            20                  25                  30

<210> SEQ ID NO 4
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 4

Tyr Lys Trp Arg Met Gly Val Tyr Leu Ser Gly Val Arg Leu Met Arg
1               5                   10                  15

Ala Phe Ile Ile
            20

<210> SEQ ID NO 5
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 5

Val Ser Tyr Arg Thr Cys Thr Ala Gly Gly Gln Met Ser Arg Trp Arg
1               5                   10                  15

Leu Phe Ile Ile
            20

<210> SEQ ID NO 6
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 6

Gly Tyr Ser Leu Thr Ser Met Ser Ala Phe Ala Val Arg Pro Cys Val
1               5                   10                  15

Cys Gly Ser Leu
            20

<210> SEQ ID NO 7
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 7

Trp Leu Gly Thr Phe Ser Gly Thr Cys Ser Thr Ala Phe Tyr Phe Pro
1               5                   10                  15
```

-continued

Leu Gly Val Pro
        20

<210> SEQ ID NO 8
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 8

Thr Asn Phe Arg Pro Ser Pro Thr Phe His Ala Ile Leu Leu Trp Pro
1               5                   10                  15

Asn Thr Phe Ser
        20

<210> SEQ ID NO 9
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 9

Val Gly Leu Gly Gly Trp Cys Phe Asp Cys Tyr Trp Val Ala Trp Asp
1               5                   10                  15

Phe Gln Thr Gln
        20

<210> SEQ ID NO 10
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 10

Phe Trp Asp Tyr Cys Gly Pro Leu Ile Cys Leu His Cys Asn Leu Gly
1               5                   10                  15

Arg Cys Val Ser
        20

<210> SEQ ID NO 11
<211> LENGTH: 5
<212> TYPE: PRT
<213> ORGANISM: Artificial Sequence
<220> FEATURE:
<223> OTHER INFORMATION: randomized peptide that bind to particular IAPs

<400> SEQUENCE: 11

Met Met Asp Ser Ala
1               5

<210> SEQ ID NO 12
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 12

Ala Ser Leu Arg Leu Tyr Pro Ile Gly Gly Thr Val Pro Phe Gly Arg
1               5                   10                  15

Thr Gly Ala Gly
        20

```
<210> SEQ ID NO 13
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 13

Gly Asp Tyr Gly Cys Cys Trp Val Val Thr Thr Gly Val Gly Val Arg
1               5                   10                  15

Cys Tyr Val Trp
            20

<210> SEQ ID NO 14
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 14

Ala Cys Trp Ala Leu Trp Ser Leu Phe Arg Gln Asp Leu Leu Leu Val
1               5                   10                  15

Ile Thr Phe Asp
            20

<210> SEQ ID NO 15
<211> LENGTH: 31
<212> TYPE: PRT
<213> ORGANISM: Artificial Sequence
<220> FEATURE:
<223> OTHER INFORMATION: randomized peptide that bind to particular IAPs

<400> SEQUENCE: 15

Asp Ser Ala Pro Gly Glu Arg Tyr Phe Val Asp Phe Leu Gly Val Ser
1               5                   10                  15

Phe Ala Cys Val Trp Ser Val Gln Asn Asp Arg Pro Asp Ser Gly
                20                  25                  30

<210> SEQ ID NO 16
<211> LENGTH: 14
<212> TYPE: PRT
<213> ORGANISM: Artificial Sequence
<220> FEATURE:
<223> OTHER INFORMATION: randomized peptide that bind to particular IAPs

<400> SEQUENCE: 16

Ile Pro Trp Ala Pro Pro Met Tyr Phe Ala Asp Ser Asn Val
1               5                   10

<210> SEQ ID NO 17
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 17

Thr Pro Ser Cys Arg Ala Gly Val Leu Arg Cys Thr Gly Cys Phe Gly
1               5                   10                  15

Val Arg Ser Gly
            20
```

```
<210> SEQ ID NO 18
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 18

Leu Trp Arg Cys Arg Thr Val Ser Ala Tyr Leu Ser Trp Leu Arg His
1               5                   10                  15

Tyr Ser Ser Ser
            20

<210> SEQ ID NO 19
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 19

His Ser Arg Pro Ala Leu Cys Met Val Ser Leu Arg Trp Ala Arg Ser
1               5                   10                  15

Leu Trp Ile Val
            20

<210> SEQ ID NO 20
<211> LENGTH: 14
<212> TYPE: PRT
<213> ORGANISM: Artificial Sequence
<220> FEATURE:
<223> OTHER INFORMATION: randomized peptide that bind to particular IAPs

<400> SEQUENCE: 20

Trp Thr His Val Trp Val Gly Trp Leu Val Ala Gly Met Ser
1               5                   10

<210> SEQ ID NO 21
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 21

Arg Phe Arg Cys Arg Ala Asp Leu Cys Val Thr Leu Thr Val Leu Ser
1               5                   10                  15

Phe Leu Ala Gln
            20

<210> SEQ ID NO 22
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 22

Cys Leu Glu Thr Leu Arg Val Cys Pro Tyr Val Ala Arg Ile Ala Ile
1               5                   10                  15

Gln His Leu Arg
            20

<210> SEQ ID NO 23
<211> LENGTH: 20
```

```
<212> TYPE: PRT
<213> ORGANISM: Artificial Sequence
<220> FEATURE:
<223> OTHER INFORMATION: randomized peptide that bind to particular IAPs

<400> SEQUENCE: 23

Leu Leu Ala Trp Arg Val Gln Gln Ser Arg Pro Leu Pro Tyr Leu His
1               5                   10                  15

Ile Ala Phe Ile
            20

<210> SEQ ID NO 24
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 24

Pro Pro Pro Leu Thr Gly Arg Trp Ser Arg Gln Cys Val Ser Val Phe
1               5                   10                  15

Gly Ile Val His
            20

<210> SEQ ID NO 25
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 25

Cys Trp Ile His Arg Ala Trp Met Leu Ser Trp His Gly Val Trp Ser
1               5                   10                  15

Leu Thr Leu Val
            20

<210> SEQ ID NO 26
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 26

Ala Pro Pro Ile Ser Gly Arg Trp Arg Gly Leu Tyr Met Arg Ser Arg
1               5                   10                  15

Phe Val Ser Leu
            20

<210> SEQ ID NO 27
<211> LENGTH: 18
<212> TYPE: PRT
<213> ORGANISM: Artificial Sequence
<220> FEATURE:
<223> OTHER INFORMATION: randomized peptide that bind to particular IAPs

<400> SEQUENCE: 27

Val Arg Leu Phe Ile Val Cys Ile Ile Ile Cys Cys Leu Met Leu Leu
1               5                   10                  15

Val Gly

<210> SEQ ID NO 28
<211> LENGTH: 20
```

```
<212> TYPE: PRT
<213> ORGANISM: Artificial Sequence
<220> FEATURE:
<223> OTHER INFORMATION: randomized peptide that bind to particular IAPs

<400> SEQUENCE: 28

Ile Pro Ser Cys Ser Val Leu Val Cys Leu Cys His Leu Ala Arg Leu
1               5                   10                  15

Trp His Cys Glu
            20

<210> SEQ ID NO 29
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 29

Cys Ser Val Met His Val Phe Arg Val Gly Pro Gly Ser Ser Gly Ser
1               5                   10                  15

Leu Ser Cys Gly
            20

<210> SEQ ID NO 30
<211> LENGTH: 42
<212> TYPE: PRT
<213> ORGANISM: Artificial Sequence
<220> FEATURE:
<223> OTHER INFORMATION: randomized peptide that bind to particular IAPs

<400> SEQUENCE: 30

Arg Ala Thr Tyr Trp Phe Arg Ser Arg Tyr Gln Val Val His Arg Ser
1               5                   10                  15

Arg Leu Pro Tyr Gly Pro Leu Ile Val Val Gly Ile Gly Ala Leu Asn
            20                  25                  30

Leu Glu Leu Asn Arg Thr Leu Leu Cys Ser
        35                  40

<210> SEQ ID NO 31
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 31

Ser Leu Ala Ile Trp Ser Thr Gln Ser Cys Ala Arg Cys Gln Cys Thr
1               5                   10                  15

Leu Ser Arg Val
            20

<210> SEQ ID NO 32
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 32

Phe Trp Phe Leu Pro Ala Pro Pro Cys Lys Cys Gly Leu Leu Tyr Arg
1               5                   10                  15

Leu Ser Val His
            20
```

<210> SEQ ID NO 33
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 33

Leu Ala Gly Arg His Phe Ser Arg Val Val Asp Arg Ile Arg Tyr Arg
1               5                   10                  15

Leu Leu Trp Thr
            20

<210> SEQ ID NO 34
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 34

Met Pro Ile Pro Pro Leu Cys Arg Ser Ala Gly Arg Leu Leu Tyr Leu
1               5                   10                  15

Tyr Thr His Tyr
            20

<210> SEQ ID NO 35
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 35

Tyr Thr Leu Pro Ser Val Leu Leu Cys Leu Met Arg Thr Gly Met Leu
1               5                   10                  15

Arg Cys Ala Cys
            20

<210> SEQ ID NO 36
<211> LENGTH: 20
<212> TYPE: PRT
<213> ORGANISM: Artificial Sequence
<220> FEATURE:
<223> OTHER INFORMATION: randomized peptide that bind to particular IAPs
<220> FEATURE:
<221> NAME/KEY: MISC_FEATURE
<222> LOCATION: (18)..(18)
<223> OTHER INFORMATION: undefined amino acid

<400> SEQUENCE: 36

Gly Met Pro Ile Arg Ala Ser Pro Cys Tyr Leu Gly Val Asp Gly Trp
1               5                   10                  15

Cys Xaa Thr Leu
            20

<210> SEQ ID NO 37
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 37

```
Lys Pro Trp Glu Tyr Leu Arg Met Phe Pro Trp Met Arg Val Ala Arg
1               5                   10                  15

Phe Phe Ile Trp
            20

<210> SEQ ID NO 38
<211> LENGTH: 20
<212> TYPE: PRT
<213> ORGANISM: Artificial Sequence
<220> FEATURE:
<223> OTHER INFORMATION: randomized peptide that bind to particular IAPs

<400> SEQUENCE: 38

Ala Leu Leu Met Phe Gly Cys Pro Asn Trp Phe Ala Ser Trp Arg Leu
1               5                   10                  15

His Leu Phe Ile
            20

<210> SEQ ID NO 39
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 39

Glu Phe Gly Ser Gly Leu Val Ser Gly Arg Gly Ile Ile Val Arg Arg
1               5                   10                  15

Met Leu Phe Leu Arg Val Leu Leu Trp Val Leu Arg Ser Ala Glu Ile
            20                  25                  30

Tyr Glu Ser
        35

<210> SEQ ID NO 40
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 40

Gly Pro Phe Glu Asn Trp Arg Val Glu Glu Leu Ala Arg Gly Arg Tyr
1               5                   10                  15

Arg Met His Gly Asp Val Val Leu Arg Ser Ala Glu Ile Tyr Glu Ser
            20                  25                  30

<210> SEQ ID NO 41
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 41

Gly Pro Ile Asp Cys Ile Ile Phe Leu Leu Trp Tyr Ser Arg Gln Gln
1               5                   10                  15

Arg Gly Gly Ser Arg Gly Gly Pro
            20

<210> SEQ ID NO 42
<211> LENGTH: 33
<212> TYPE: PRT
<213> ORGANISM: Artificial Sequence
<220> FEATURE:
```

-continued

<223> OTHER INFORMATION: randomized peptide that bind to particular IAPs

<400> SEQUENCE: 42

Gly Ser Arg Phe Arg Val Phe Val Cys Ser Leu Phe Ser Phe Leu Ser
1               5                   10                  15

Gly Arg Gly Gly Gly Val Val Val Leu Arg Ser Ala Glu Ile Tyr Glu
            20                  25                  30

Ser

<210> SEQ ID NO 43
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 43

Gly Pro Phe Lys Arg Cys His Glu Arg Leu Val Ala Phe Ala Arg Cys
1               5                   10                  15

Trp Phe Met Trp Ser Met Val Leu Arg Ser Ala Glu Ile Tyr Glu Ser
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 44

Gly Pro Ser Asn Asp Asn Gln Leu Val Leu Arg Val Arg Ile Leu Arg
1               5                   10                  15

Val Leu Ile Val Met Arg Val Leu Arg Ser Ala Glu Ile Tyr Glu Ser
            20                  25                  30

<210> SEQ ID NO 45
<211> LENGTH: 27
<212> TYPE: PRT
<213> ORGANISM: Artificial Sequence
<220> FEATURE:
<223> OTHER INFORMATION: randomized peptide that bind to particular IAPs

<400> SEQUENCE: 45

Glu Phe Arg Val Arg Arg Met Arg Leu Leu Val Arg Leu Met Gly Ser
1               5                   10                  15

Asp Asp Ser Gly Thr Ile Pro Asp Phe Gly Pro
            20                  25

<210> SEQ ID NO 46
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 46

Gly Pro Ser Leu Gln Phe Leu Glu Val Val Ser Cys Tyr Met Val
1               5                   10                  15

Leu Tyr Asp Leu Ser Lys Gly Pro
            20

<210> SEQ ID NO 47
<211> LENGTH: 34

```
<212> TYPE: PRT
<213> ORGANISM: Artificial Sequence
<220> FEATURE:
<223> OTHER INFORMATION: randomized peptide that bind to particular IAPs

<400> SEQUENCE: 47

Gly Pro Gln Pro Phe Cys Ser Pro Pro Ser Phe Tyr Thr Arg Leu Leu
1               5                   10                  15

Ile Ile Val Arg Leu Leu Ser Leu Asp Leu Gln Arg Ser Ser Asn Arg
            20                  25                  30

Arg Tyr

<210> SEQ ID NO 48
<211> LENGTH: 23
<212> TYPE: PRT
<213> ORGANISM: Artificial Sequence
<220> FEATURE:
<223> OTHER INFORMATION: randomized peptide that bind to particular IAPs

<400> SEQUENCE: 48

Gly Pro Ala Pro Leu Ser Leu Cys Val Cys Lys Cys Gly Cys Gly His
1               5                   10                  15

Thr Arg Pro Phe Val Gly Pro
            20

<210> SEQ ID NO 49
<211> LENGTH: 21
<212> TYPE: PRT
<213> ORGANISM: Artificial Sequence
<220> FEATURE:
<223> OTHER INFORMATION: randomized peptide that bind to particular IAPs

<400> SEQUENCE: 49

Gly Pro Asp Val His Ile Trp Gln Ser Ile Ile Phe Tyr Ala Met Arg
1               5                   10                  15

His Met Met Gly Pro
            20

<210> SEQ ID NO 50
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 50

Glu Phe Gly Ser Gly Cys Gly Cys Phe Val Arg Gly Arg Ile Val Arg
1               5                   10                  15

Ile Arg Cys Val Ile Leu Leu Leu Arg Val Leu Arg Ser Ala Glu Ile
            20                  25                  30

Tyr Glu Ser
        35

<210> SEQ ID NO 51
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 51

Gly Pro His Ser Ser Ala His Asp Arg Ile Trp Leu Arg Val Arg Gly
1               5                   10                  15
```

-continued

Leu Arg Ile Ile Leu Leu Val Leu Arg Ser Ala Glu Ile Tyr Glu Ser
                20                  25                  30

<210> SEQ ID NO 52
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 52

Glu Phe Gly Ser Gly Leu Cys Val Arg Arg Trp Trp Gly Met Ser Val
1               5                   10                  15

Gly Ser Arg Ile Met Leu Val Met Leu Val Leu Arg Ser Ala Glu Ile
            20                  25                  30

Tyr Glu Ser
        35

<210> SEQ ID NO 53
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 53

Gly Pro Val Tyr Ser Glu Ala Phe Val Cys Leu Val Cys Ala Gly Val
1               5                   10                  15

Cys Val Glu Glu Cys Gly Gly Ser Leu Asp Leu Gln Arg Ser Ser Asn
            20                  25                  30

Arg Arg Tyr
        35

<210> SEQ ID NO 54
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 54

Gly Pro Ile Glu Thr Val Gly Phe Ile Val Arg Leu His Thr Leu Leu
1               5                   10                  15

Met Val Leu Arg Arg Thr Gly Pro
            20

<210> SEQ ID NO 55
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 55

Gly Pro Leu His Arg Thr Leu Leu Val Asp Met Cys Cys Trp Leu Met
1               5                   10                  15

Ser Leu Glu Ser Asn Met Gly Pro
            20

<210> SEQ ID NO 56
<211> LENGTH: 35
<212> TYPE: PRT
<213> ORGANISM: Artificial Sequence
<220> FEATURE:

-continued

<223> OTHER INFORMATION: randomized peptide that bind to particular IAPs

<400> SEQUENCE: 56

Glu Phe Gly Val Arg Val Val Cys Val Val Arg Ser Leu Phe Val Leu
1               5                   10                  15

Arg Cys Gly Leu Leu Arg Cys Arg Gly Val Leu Arg Ser Ala Glu Ile
            20                  25                  30

Tyr Glu Ser
        35

<210> SEQ ID NO 57
<211> LENGTH: 34
<212> TYPE: PRT
<213> ORGANISM: Artificial Sequence
<220> FEATURE:
<223> OTHER INFORMATION: randomized peptide that bind to particular IAPs

<400> SEQUENCE: 57

Glu Phe Val Arg Glu Cys Ser Leu Cys Arg Val Met Val Leu Met Phe
1               5                   10                  15

Val Leu Arg Gly Ile Arg Leu Arg Val Leu Arg Ser Ala Glu Ile Tyr
            20                  25                  30

Glu Ser

<210> SEQ ID NO 58
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 58

Glu Phe Gly Val Arg Leu Leu Val Leu Leu Arg Leu Arg Cys Val Arg
1               5                   10                  15

Arg Gly Gly Gly Cys Phe Val Cys Trp Val Leu Arg Ser Ala Glu Ile
            20                  25                  30

Tyr Glu Ser
        35

<210> SEQ ID NO 59
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 59

Gly Ser Gly Phe Arg Met Arg Val Leu Val Met Val Cys Arg Leu Arg
1               5                   10                  15

Val Val Phe Leu Val Arg Arg Val Leu Arg Ser Ala Glu Ile Tyr Glu
            20                  25                  30

Ser

<210> SEQ ID NO 60
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 60

Gly Arg Leu Gly Trp Leu Arg Leu Leu Cys Val Arg Ile Val Leu Val

```
                1               5                  10                 15
Cys Leu Arg Arg Gly Leu Val Leu Arg Ser Ala Glu Ile Tyr Glu Ser
            20                  25                 30

<210> SEQ ID NO 61
<211> LENGTH: 37
<212> TYPE: PRT
<213> ORGANISM: Artificial Sequence
<220> FEATURE:
<223> OTHER INFORMATION: randomized peptide that bind to particular IAPs

<400> SEQUENCE: 61

Glu Phe Gly Ser Gly Trp Tyr Val Asp Leu Gly Asp Tyr Ser Val Trp
1               5                  10                 15

Val Asp Tyr Val Tyr Cys Gly Ser Gly Ser Leu Asp Leu Gln Arg Ser
            20                  25                 30

Ser Asn Arg Arg Tyr
        35

<210> SEQ ID NO 62
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 62

Gly Pro Ser Gln Cys Ala Gln Arg Val Ala Leu Ile Gln Met Tyr Ile
1               5                  10                 15

Asp Ala Leu Val Cys Ile Gly Pro
            20

<210> SEQ ID NO 63
<211> LENGTH: 35
<212> TYPE: PRT
<213> ORGANISM: Artificial Sequence
<220> FEATURE:
<223> OTHER INFORMATION: randomized peptide that bind to particular IAPs
<220> FEATURE:
<221> NAME/KEY: MISC_FEATURE
<222> LOCATION: (19)..(19)
<223> OTHER INFORMATION: undefined amino acid

<400> SEQUENCE: 63

Glu Phe Gly Ser Gly Cys Val Arg Ile Arg Val Gly Ile Val Arg Arg
1               5                  10                 15

Met Leu Xaa Leu Arg Phe Val Phe Leu Val Leu Arg Ser Ala Glu Ile
            20                  25                 30

Tyr Glu Ser
        35

<210> SEQ ID NO 64
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 64

Gly Pro Leu Leu Asp Pro Met Leu Arg Gln Arg Phe Ser Leu Arg Val
1               5                  10                 15

Trp Ile Met Leu Leu Gly Val Leu Arg Ser Ala Glu Ile Tyr Glu Ser
            20                  25                 30
```

```
<210> SEQ ID NO 65
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 65

Gly Pro Asn Ser Trp Val Trp Arg Tyr Val Thr Ile Ala His Trp Leu
1               5                   10                  15

Ala Asn Tyr Arg Met Ser Gly Pro
            20

<210> SEQ ID NO 66
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 66

Gly Pro Ala Met Lys Ser Cys Thr Ile Arg Val Phe Arg Val Cys Ile
1               5                   10                  15

Val Leu Arg Ile Val Arg Val Leu Arg Ser Ala Glu Ile Tyr Glu Ser
            20                  25                  30

<210> SEQ ID NO 67
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 67

Glu Phe Gly Val Arg Met Arg Leu Met Ile Arg Ile Phe Arg Gly Leu
1               5                   10                  15

Phe Val Leu Arg Gly Phe Arg Gly Leu Val Leu Arg Ser Ala Glu Ile
            20                  25                  30

Tyr Glu Ser
        35

<210> SEQ ID NO 68
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 68

Gly Pro Val Pro Ser Ser Pro Cys Ser Phe Leu Leu Tyr Cys Arg Asp
1               5                   10                  15

Val Leu Cys His Trp Pro Gly Pro
            20

<210> SEQ ID NO 69
<211> LENGTH: 26
<212> TYPE: PRT
<213> ORGANISM: Artificial Sequence
<220> FEATURE:
<223> OTHER INFORMATION: randomized peptide that bind to particular IAPs

<400> SEQUENCE: 69

Gly Pro Cys Glu Pro Phe Ile Gly Asp Cys Trp Pro Cys Leu Ile Arg
1               5                   10                  15
```

```
Thr Leu Val Thr Leu Arg Gly Leu Asp Leu
            20                  25

<210> SEQ ID NO 70
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 70

Gly Pro Trp Trp Lys Asp Arg Gly Val Leu Val Arg Leu Cys Val Leu
1               5                   10                  15

Arg Leu Val Val Gly Val Val Leu Arg Ser Ala Glu Ile Tyr Glu Ser
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: randomized peptide that bind to particular IAPs
<220> FEATURE:
<221> NAME/KEY: MISC_FEATURE
<222> LOCATION: (18)..(18)
<223> OTHER INFORMATION: undefined amino acid

<400> SEQUENCE: 71

Gly Pro Arg Leu Leu Val Arg Met Arg Gly Trp Cys Arg Val Ser Leu
1               5                   10                  15

Ile Xaa Phe Trp Leu Arg Val Leu Arg Ser Ala Glu Ile Tyr Glu Ser
            20                  25                  30

<210> SEQ ID NO 72
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 72

Glu Phe Arg Val Arg Ile Ile Val Val Ser Leu Arg Ile Trp Arg Leu
1               5                   10                  15

Leu Val Arg Arg Arg Cys Leu Cys Leu Val Leu Arg Ser Ala Glu Ile
            20                  25                  30

Tyr Glu Ser
        35

<210> SEQ ID NO 73
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 73

Gly Pro Val Glu Cys Ala Asp Val Leu Phe Ala Ser Arg Ile Arg Leu
1               5                   10                  15

Leu Cys Leu Cys Phe Arg Val Leu Arg Ser Ala Glu Ile Tyr Glu Ser
            20                  25                  30

<210> SEQ ID NO 74
<211> LENGTH: 34
<212> TYPE: PRT
```

<213> ORGANISM: Artificial Sequence
<220> FEATURE:
<223> OTHER INFORMATION: randomized peptide that bind to particular IAPs

<400> SEQUENCE: 74

Glu Phe Gly Arg Arg Leu Leu Val Phe Arg Leu Ser Val Phe Val Val
1               5                   10                  15

Val Leu Gly Arg Arg Leu Ser Arg Val Leu Arg Ser Ala Glu Ile Tyr
            20                  25                  30

Glu Ser

<210> SEQ ID NO 75
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 75

Gly Ala Gly Leu Gly Arg Val Ile Arg Leu Arg Ile Val Val Leu Arg
1               5                   10                  15

Cys Ile Phe Leu Leu Phe Arg Val Leu Arg Ser Ala Glu Ile Tyr Glu
            20                  25                  30

Ser

<210> SEQ ID NO 76
<211> LENGTH: 28
<212> TYPE: PRT
<213> ORGANISM: Artificial Sequence
<220> FEATURE:
<223> OTHER INFORMATION: randomized peptide that bind to particular IAPs

<400> SEQUENCE: 76

Gly Pro Phe Pro Phe Asp Tyr Pro Arg Trp Ile Met Ile Val Leu Leu
1               5                   10                  15

Arg Gly Val Leu Arg Ser Ala Glu Ile Tyr Glu Ser
            20                  25

<210> SEQ ID NO 77
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 77

Gly Ser Arg Gly Leu Arg Leu Cys Leu Leu Gly Arg Cys Arg Leu Cys
1               5                   10                  15

Gly Cys Leu Ile Ile Met Arg Val Leu Arg Ser Ala Glu Ile Tyr Glu
            20                  25                  30

Ser

<210> SEQ ID NO 78
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 78

Gly Pro Glu Ser Tyr Val Leu Trp Pro Ala Arg Gly Glu Ala Leu Tyr
1               5                   10                  15

Tyr Leu Arg Ala Trp Leu Gly Pro
            20

<210> SEQ ID NO 79
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 79

Gly Ser Arg Cys Ile Arg Arg Arg Ile Ser Ile Leu Phe Phe Val Phe
1               5                   10                  15

Arg Val Leu Arg Ser Arg Arg Val Leu Arg Ser Ala Glu Ile Tyr Glu
            20                  25                  30

Ser

<210> SEQ ID NO 80
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 80

Gly Pro Phe Ser Glu His Ala Arg Gly His Val Val Thr Ile Cys Arg
1               5                   10                  15

Leu Arg Leu Leu Phe Trp Leu Leu Arg Ser Ala Glu Ile Tyr Glu Ser
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 81

Gly Pro Ser Ser Leu Leu Arg Arg Cys Leu Ile Leu Gly Met Val Leu
1               5                   10                  15

Gly Val Leu Arg Arg Arg Val Leu Arg Ser Ala Glu Ile Tyr Glu Ser
            20                  25                  30

<210> SEQ ID NO 82
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 82

Gly Pro His Pro Val Leu Ala Val Gln Leu Ile Asn Ala Tyr Leu Gly
1               5                   10                  15

Leu Glu Arg Val Gly Arg Gly Pro
            20

<210> SEQ ID NO 83
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 83

-continued

```
Gly Pro Leu Pro Ser Gly Ala Val Ser Thr Glu Ala Tyr Phe Trp Glu
1               5                   10                  15

Val Phe Lys Leu Leu Met Gly Pro
            20
```

<210> SEQ ID NO 84
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 84

```
Gly Pro Tyr Pro Tyr Leu Arg Ile Leu Leu Val Gln Lys Ile Ala Cys
1               5                   10                  15

Val Arg Arg Ala Leu Trp Val Leu Arg Ser Ala Glu Ile Tyr Glu Ser
            20                  25                  30
```

<210> SEQ ID NO 85
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 85

```
Gly Pro Val Gly Val Glu Gly Val Asp Ser Val Phe Gly Trp Cys Val
1               5                   10                  15

Val Cys Phe Leu Leu Val Trp Ser Leu Asp Leu Gln Arg Ser Ser Asn
            20                  25                  30

Arg Arg Tyr
        35
```

<210> SEQ ID NO 86
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 86

```
Glu Phe Arg Val Arg Val Leu Gly Cys Met Gly Val Phe Leu Arg Leu
1               5                   10                  15

Arg Phe Cys Gly Gly Leu Arg Leu Arg Val Leu Arg Ser Ala Glu Ile
            20                  25                  30

Tyr Glu Ser
        35
```

<210> SEQ ID NO 87
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 87

```
Gly Ser Gly Leu Val Ser Gly Arg Gly Ile Ile Val Arg Arg Met Leu
1               5                   10                  15

Phe Leu Arg Val Leu Leu Trp Val Leu Arg Ser Ala Glu Ile Tyr Glu
            20                  25                  30

Ser
```

```
<210> SEQ ID NO 88
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 88

Gly Pro Phe Glu Asn Trp Arg Val Glu Glu Leu Ala Arg Gly Arg Tyr
1               5                   10                  15

Arg Met His Gly Asp Val Val Leu Arg Ser Ala Glu Ile Tyr Glu Ser
            20                  25                  30

<210> SEQ ID NO 89
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 89

Gly Pro Ile Asp Cys Ile Ile Phe Leu Leu Trp Tyr Ser Arg Gln Gln
1               5                   10                  15

Arg Gly Gly Ser Arg Gly Gly Pro
            20

<210> SEQ ID NO 90
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 90

Gly Ser Arg Phe Arg Val Phe Val Cys Ser Leu Phe Ser Phe Leu Ser
1               5                   10                  15

Gly Arg Gly Gly Gly Val Val Leu Arg Ser Ala Glu Ile Tyr Glu
            20                  25                  30

Ser

<210> SEQ ID NO 91
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 91

Gly Pro Phe Lys Arg Cys His Glu Arg Leu Val Ala Phe Ala Arg Cys
1               5                   10                  15

Trp Phe Met Trp Ser Met Val Leu Arg Ser Ala Glu Ile Tyr Glu Ser
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 92

Gly Pro Ser Asn Asp Asn Gln Leu Val Leu Arg Val Arg Ile Leu Arg
1               5                   10                  15

Val Leu Ile Val Met Arg Val Leu Arg Ser Ala Glu Ile Tyr Glu Ser
```

```
                   20                  25                  30

<210> SEQ ID NO 93
<211> LENGTH: 25
<212> TYPE: PRT
<213> ORGANISM: Artificial Sequence
<220> FEATURE:
<223> OTHER INFORMATION: randomized peptide that bind to particular IAPs

<400> SEQUENCE: 93

Arg Val Arg Arg Met Arg Leu Leu Val Arg Leu Met Gly Ser Asp Asp
1               5                   10                  15

Ser Gly Thr Ile Pro Asp Phe Gly Pro
            20                  25

<210> SEQ ID NO 94
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 94

Gly Pro Ser Leu Gln Phe Leu Glu Val Val Ser Cys Tyr Met Val
1               5                   10                  15

Leu Tyr Asp Leu Ser Lys Gly Pro
            20

<210> SEQ ID NO 95
<211> LENGTH: 34
<212> TYPE: PRT
<213> ORGANISM: Artificial Sequence
<220> FEATURE:
<223> OTHER INFORMATION: randomized peptide that bind to particular IAPs

<400> SEQUENCE: 95

Gly Pro Gln Pro Phe Cys Ser Pro Pro Ser Phe Tyr Thr Arg Leu Leu
1               5                   10                  15

Ile Ile Val Arg Leu Leu Ser Leu Asp Leu Gln Arg Ser Ser Asn Arg
            20                  25                  30

Arg Tyr

<210> SEQ ID NO 96
<211> LENGTH: 23
<212> TYPE: PRT
<213> ORGANISM: Artificial Sequence
<220> FEATURE:
<223> OTHER INFORMATION: randomized peptide that bind to particular IAPs

<400> SEQUENCE: 96

Gly Pro Ala Pro Leu Ser Leu Cys Val Cys Lys Cys Gly Cys Gly His
1               5                   10                  15

Thr Arg Pro Phe Val Gly Pro
            20

<210> SEQ ID NO 97
<211> LENGTH: 21
<212> TYPE: PRT
<213> ORGANISM: Artificial Sequence
<220> FEATURE:
<223> OTHER INFORMATION: randomized peptide that bind to particular IAPs

<400> SEQUENCE: 97

Gly Pro Asp Val His Ile Trp Gln Ser Ile Ile Phe Tyr Ala Met Arg
```

```
1               5                  10                 15
His Met Met Gly Pro
                20
```

<210> SEQ ID NO 98
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 98

```
Gly Ser Gly Cys Gly Cys Phe Val Arg Gly Arg Ile Val Arg Ile Arg
1               5                   10                  15
Cys Val Ile Leu Leu Leu Arg Val Leu Arg Ser Ala Glu Ile Tyr Glu
                20                  25                  30
Ser
```

<210> SEQ ID NO 99
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 99

```
Gly Pro His Ser Ser Ala His Asp Arg Ile Trp Leu Arg Val Arg Gly
1               5                   10                  15
Leu Arg Ile Ile Leu Leu Val Leu Arg Ser Ala Glu Ile Tyr Glu Ser
                20                  25                  30
```

<210> SEQ ID NO 100
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 100

```
Gly Ser Gly Leu Cys Val Arg Arg Trp Trp Gly Met Ser Val Gly Ser
1               5                   10                  15
Arg Ile Met Leu Val Met Leu Val Leu Arg Ser Ala Glu Ile Tyr Glu
                20                  25                  30
Ser
```

<210> SEQ ID NO 101
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 101

```
Gly Pro Val Tyr Ser Glu Ala Phe Val Cys Leu Val Cys Ala Gly Val
1               5                   10                  15
Cys Val Glu Glu Cys Gly Gly Ser Leu Asp Leu Gln Arg Ser Ser Asn
                20                  25                  30
Arg Arg Tyr
        35
```

<210> SEQ ID NO 102
<211> LENGTH: 24

```
<212> TYPE: PRT
<213> ORGANISM: Artificial Sequence
<220> FEATURE:
<223> OTHER INFORMATION: randomized peptide that bind to particular IAPs

<400> SEQUENCE: 102

Gly Pro Ile Glu Thr Val Gly Phe Ile Val Arg Leu His Thr Leu Leu
1               5                   10                  15

Met Val Leu Arg Arg Thr Gly Pro
            20

<210> SEQ ID NO 103
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 103

Gly Pro Leu His Arg Thr Leu Leu Val Asp Met Cys Cys Trp Leu Met
1               5                   10                  15

Ser Leu Glu Ser Asn Met Gly Pro
            20

<210> SEQ ID NO 104
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 104

Gly Val Arg Val Val Cys Val Val Arg Ser Leu Phe Val Leu Arg Cys
1               5                   10                  15

Gly Leu Leu Arg Cys Arg Gly Val Leu Arg Ser Ala Glu Ile Tyr Glu
            20                  25                  30

Ser

<210> SEQ ID NO 105
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 105

Val Arg Glu Cys Ser Leu Cys Arg Val Met Val Leu Met Phe Val Leu
1               5                   10                  15

Arg Gly Ile Arg Leu Arg Val Leu Arg Ser Ala Glu Ile Tyr Glu Ser
            20                  25                  30

<210> SEQ ID NO 106
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 106

Gly Val Arg Leu Leu Val Leu Leu Arg Leu Arg Cys Val Arg Arg Gly
1               5                   10                  15

Gly Gly Cys Phe Val Cys Trp Val Leu Arg Ser Ala Glu Ile Tyr Glu
            20                  25                  30
```

Ser

```
<210> SEQ ID NO 107
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 107
```

Gly Ser Gly Phe Arg Met Arg Val Leu Val Met Val Cys Arg Leu Arg
1               5                   10                  15

Val Val Phe Leu Val Arg Arg Val Leu Arg Ser Ala Glu Ile Tyr Glu
            20                  25                  30

Ser

```
<210> SEQ ID NO 108
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 108
```

Gly Arg Leu Gly Trp Leu Arg Leu Leu Cys Val Arg Ile Val Leu Val
1               5                   10                  15

Cys Leu Arg Arg Gly Leu Val Leu Arg Ser Ala Glu Ile Tyr Glu Ser
            20                  25                  30

```
<210> SEQ ID NO 109
<211> LENGTH: 35
<212> TYPE: PRT
<213> ORGANISM: Artificial Sequence
<220> FEATURE:
<223> OTHER INFORMATION: randomized peptide that bind to particular IAPs

<400> SEQUENCE: 109
```

Gly Ser Gly Trp Tyr Val Asp Leu Gly Asp Tyr Ser Val Trp Val Asp
1               5                   10                  15

Tyr Val Tyr Cys Gly Ser Gly Ser Leu Asp Leu Gln Arg Ser Ser Asn
            20                  25                  30

Arg Arg Tyr
        35

```
<210> SEQ ID NO 110
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 110
```

Gly Pro Ser Gln Cys Ala Gln Arg Val Ala Leu Ile Gln Met Tyr Ile
1               5                   10                  15

Asp Ala Leu Val Cys Ile Gly Pro
            20

```
<210> SEQ ID NO 111
<211> LENGTH: 25
<212> TYPE: PRT
<213> ORGANISM: Artificial Sequence
<220> FEATURE:
<223> OTHER INFORMATION: randomized peptide that bind to particular IAPs
```

```
<400> SEQUENCE: 111

Gly Ser Gly Cys Val Arg Ile Arg Val Gly Ile Val Arg Arg Met Leu
1               5                   10                  15

Phe Leu Arg Phe Val Phe Leu Val Pro
            20                  25

<210> SEQ ID NO 112
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 112

Gly Pro Leu Leu Asp Pro Met Leu Arg Gln Arg Phe Ser Leu Arg Val
1               5                   10                  15

Trp Ile Met Leu Leu Gly Val Leu Arg Ser Ala Glu Ile Tyr Glu Ser
            20                  25                  30

<210> SEQ ID NO 113
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 113

Gly Pro Asn Ser Trp Val Trp Arg Tyr Val Thr Ile Ala His Trp Leu
1               5                   10                  15

Ala Asn Tyr Arg Met Ser Gly Pro
            20

<210> SEQ ID NO 114
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 114

Gly Pro Ala Met Lys Ser Cys Thr Ile Arg Val Phe Arg Val Cys Ile
1               5                   10                  15

Val Leu Arg Ile Val Arg Val Leu Arg Ser Ala Glu Ile Tyr Glu Ser
            20                  25                  30

<210> SEQ ID NO 115
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 115

Gly Val Arg Met Arg Leu Met Ile Arg Ile Phe Arg Gly Leu Phe Val
1               5                   10                  15

Leu Arg Gly Phe Arg Gly Leu Val Leu Arg Ser Ala Glu Ile Tyr Glu
            20                  25                  30

Ser

<210> SEQ ID NO 116
<211> LENGTH: 24
<212> TYPE: PRT
<213> ORGANISM: Artificial Sequence
```

```
<220> FEATURE:
<223> OTHER INFORMATION: randomized peptide that bind to particular IAPs

<400> SEQUENCE: 116

Gly Pro Val Pro Ser Ser Pro Cys Ser Phe Leu Leu Tyr Cys Arg Asp
1               5                   10                  15

Val Leu Cys His Trp Pro Gly Pro
            20

<210> SEQ ID NO 117
<211> LENGTH: 34
<212> TYPE: PRT
<213> ORGANISM: Artificial Sequence
<220> FEATURE:
<223> OTHER INFORMATION: randomized peptide that bind to particular IAPs

<400> SEQUENCE: 117

Gly Pro Cys Glu Pro Phe Ile Gly Asp Cys Trp Pro Cys Leu Ile Arg
1               5                   10                  15

Thr Leu Val Thr Leu Arg Gly Leu Asp Leu Gln Arg Ser Ser Asn Arg
            20                  25                  30

Arg Tyr

<210> SEQ ID NO 118
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 118

Gly Pro Trp Trp Lys Asp Arg Gly Val Leu Val Arg Leu Cys Val Leu
1               5                   10                  15

Arg Leu Val Val Gly Val Val Leu Arg Ser Ala Glu Ile Tyr Glu Ser
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: randomized peptide that bind to particular IAPs
<220> FEATURE:
<221> NAME/KEY: MISC_FEATURE
<222> LOCATION: (18)..(18)
<223> OTHER INFORMATION: undefined amino acid

<400> SEQUENCE: 119

Gly Pro Arg Leu Leu Val Arg Met Arg Gly Trp Cys Arg Val Ser Leu
1               5                   10                  15

Ile Xaa Phe Trp Leu Arg Val Leu Arg Ser Ala Glu Ile Tyr Glu Ser
            20                  25                  30

<210> SEQ ID NO 120
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 120

Arg Val Arg Ile Ile Val Val Ser Leu Arg Ile Trp Arg Leu Leu Val
1               5                   10                  15

Arg Arg Arg Cys Leu Cys Leu Val Leu Arg Ser Ala Glu Ile Tyr Glu
```

-continued

```
                20                  25                  30

Ser

<210> SEQ ID NO 121
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 121

Gly Pro Val Glu Cys Ala Asp Val Leu Phe Ala Ser Arg Ile Arg Leu
1               5                   10                  15

Leu Cys Leu Cys Phe Arg Val Leu Arg Ser Ala Glu Ile Tyr Glu Ser
                20                  25                  30

<210> SEQ ID NO 122
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 122

Gly Arg Arg Leu Leu Val Phe Arg Leu Ser Val Phe Val Val Val Leu
1               5                   10                  15

Gly Arg Arg Leu Ser Arg Val Leu Arg Ser Ala Glu Ile Tyr Glu Ser
                20                  25                  30

<210> SEQ ID NO 123
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 123

Gly Ala Gly Leu Gly Arg Val Ile Arg Leu Arg Ile Val Val Leu Arg
1               5                   10                  15

Cys Ile Phe Leu Leu Phe Arg Val Leu Arg Ser Ala Glu Ile Tyr Glu
                20                  25                  30

Ser

<210> SEQ ID NO 124
<211> LENGTH: 28
<212> TYPE: PRT
<213> ORGANISM: Artificial Sequence
<220> FEATURE:
<223> OTHER INFORMATION: randomized peptide that bind to particular IAPs

<400> SEQUENCE: 124

Gly Pro Phe Pro Phe Asp Tyr Pro Arg Trp Ile Met Ile Val Leu Leu
1               5                   10                  15

Arg Gly Val Leu Arg Ser Ala Glu Ile Tyr Glu Ser
                20                  25

<210> SEQ ID NO 125
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 125
```

-continued

```
Gly Ser Arg Gly Leu Arg Leu Cys Leu Leu Gly Arg Cys Arg Leu Cys
1               5                   10                  15

Gly Cys Leu Ile Ile Met Arg Val Leu Arg Ser Ala Glu Ile Tyr Glu
            20                  25                  30

Ser

<210> SEQ ID NO 126
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 126

Gly Pro Glu Ser Tyr Val Leu Trp Pro Ala Arg Gly Glu Ala Leu Tyr
1               5                   10                  15

Tyr Leu Arg Ala Trp Leu Gly Pro
            20

<210> SEQ ID NO 127
<211> LENGTH: 33
<212> TYPE: PRT
<213> ORGANISM: Artificial Sequence
<220> FEATURE:
<223> OTHER INFORMATION: randomized peptide that bind to particular IAPs

<400> SEQUENCE: 127

Gly Ser Arg Cys Ile Arg Arg Ile Ser Ile Leu Phe Phe Val Phe
1               5                   10                  15

Arg Val Leu Arg Ser Arg Arg Val Leu Arg Ser Ala Glu Ile Tyr Glu
            20                  25                  30

Ser

<210> SEQ ID NO 128
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 128

Gly Pro Phe Ser Glu His Ala Arg Gly His Val Val Thr Ile Cys Arg
1               5                   10                  15

Leu Arg Leu Leu Phe Trp Leu Leu Arg Ser Ala Glu Ile Tyr Glu Ser
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 129

Gly Pro Ser Ser Leu Leu Arg Arg Cys Leu Ile Leu Gly Met Val Leu
1               5                   10                  15

Gly Val Leu Arg Arg Arg Val Leu Arg Ser Ala Glu Ile Tyr Glu Ser
            20                  25                  30

<210> SEQ ID NO 130
<211> LENGTH: 24
<212> TYPE: PRT
```

```
<213> ORGANISM: Artificial Sequence
<220> FEATURE:
<223> OTHER INFORMATION: randomized peptide that bind to particular IAPs

<400> SEQUENCE: 130

Gly Pro His Pro Val Leu Ala Val Gln Leu Ile Asn Ala Tyr Leu Gly
1               5                   10                  15

Leu Glu Arg Val Gly Arg Gly Pro
            20

<210> SEQ ID NO 131
<211> LENGTH: 24
<212> TYPE: PRT
<213> ORGANISM: Artificial Sequence
<220> FEATURE:
<223> OTHER INFORMATION: randomized peptide that bind to particular IAPs

<400> SEQUENCE: 131

Gly Pro Leu Pro Ser Gly Ala Val Ser Thr Glu Ala Tyr Phe Trp Glu
1               5                   10                  15

Val Phe Lys Leu Leu Met Gly Pro
            20

<210> SEQ ID NO 132
<211> LENGTH: 32
<212> TYPE: PRT
<213> ORGANISM: Artificial Sequence
<220> FEATURE:
<223> OTHER INFORMATION: randomized peptide that bind to particular IAPs

<400> SEQUENCE: 132

Gly Pro Tyr Pro Tyr Leu Arg Ile Leu Leu Val Gln Lys Ile Ala Cys
1               5                   10                  15

Val Arg Arg Ala Leu Trp Val Leu Arg Ser Ala Glu Ile Tyr Glu Ser
            20                  25                  30
```

PEPTIDES FOR INDUCING APOPTOSIS IN TUMOR CELLS

The present invention relates to peptides that are suitable to induce apoptosis, the nucleic acids encoding said peptides and the use of the peptides and/or nucleic acids in cancer therapy.

Cancer is the second major cause of death in Europe and Northern America. The effective cure of patients, though, is often difficult since many tumor cells have developed a resistance to anti-cancer drugs used for chemotherapy. The described phenotype involves a variety of strategies that tumor cells use to evade the cytostatic effects of anticancer drugs. Mechanisms for drug resistance include modifications in detoxification and DNA repair pathways, changes in cellular sites of drug sequestration, decreases in drug-target affinity, synthesis of specific drug inhibitors within cells, and accelerated removal or secretion of drugs. Cancer cells commonly fail to undergo so-called "programmed cell death" or "apoptosis", a signaling process that plays a key role in preventing cell tissues from abnormal growth. Thus, apoptosis defects appear to be a major problem in cancer therapy as they confer resistance to many tumors against current treatment protocols, leading to tumor progression.

Apoptosis pathways involve diverse groups of molecules. One set of mediators implicated in apoptosis are so-called caspases, cysteine proteases that cleave their substrates specifically at aspartate residues. Caspases convey the apoptotic signal in a proteolytic cascade, with caspases cleaving and activating other caspases which subsequently degrade other cellular targets eventually resulting in cellular breakdown. If one or more steps in this cascade is inhibited in tumor cells, these cells fail to accomplish apoptosis and, thus, continue to grow. Caspase activation itself can be triggered by external stimuli or by intracellular stress response via the mitochondria leading to the release of mitochondrial proteins.

A failure in activating the caspase cascade is caused by the action of so-called Inhibitors of Apoptosis Proteins (IAPs). IAPs bind to early active caspases, thereby preventing the ongoing of the apoptosis process. They are expressed at high levels in many tumors and, by inhibition of caspases, contribute to the resistance of cancers against apoptosis induction.

From the foregoing it becomes evident, that inhibition of IAP function represents a major task for efficient cancer therapy. It has been reported earlier that the mammalian mitochondrial protein Smac, when released into the cytosol in the course of an apoptotic response, can bind to IAPs and, thus, promotes the proteolytic activation of caspases resulting in apoptosis. Therefore, Smac or fragments thereof, could be a potential tool for the treatment of drug-resistant tumors. However, the therapeutic use of naturally existing IAP-binding proteins like Smac can bear the disadvantage of evoking undesired side effects. In addition, binding of Smac to IAPs is restricted to a particular region on the IAP protein, the so-called BIR region. The problem underlying the present invention is to find other molecules which are able to promote apoptosis in tumor cells by binding to IAPs, but which do not possess the disadvantages of naturally existing IAP-binding partners.

Peptides that bind to IAPs, in particular to the BIR region of IAPs are known to the person skilled in the art. WO-A 02/16402 discloses aminoterminal Smac peptides (so-called AV peptoides) which bind to IAPs and abolish their inhibitory effect. The amino acid sequence of these peptides follows a distinct order, namely that the first amino acid is an alanin, the second amino acid is preferably a valin, isoleucin or leucin, and the third amino acid is preferably a prolin or an alanin. WO-A 02/26775 discloses synthetic tetrapeptides, which also bind specifically to the BIR domain of IAPs. The disclosed amino acid sequence of the tetrapeptides follows the order of alanine, valin (or threonin or isoleucin), prolin (or alanin), phenylalanine (or tyrosin or isoleucin or valin). The problem of the present invention is to find peptides, that do inhibit the function of IAPs via a different mechanism.

The present invention solves the described problem by providing randomized peptides that bind to particular IAPs and, thus, can impede said IAPs from exerting their anti-apoptotic effect.

The object of the present invention is attained by a peptide, a fragment or derivative thereof, comprising an amino acid sequence selected from the group of SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86. (see TABLE 1).

In the context of the present invention, the term derivative or fragment of peptides further includes peptides in which one or more amino acids of the disclosed sequences can be substituted by one or more amino acids different from the original one(s), or peptides the amino acid sequence of which is either extended, shortened, or both, on either the aminoterminal, or the carboxyterminal or both ends with respect to the original proteins, provided that the binding properties of the peptides remain unaffected. Preferably they differ from the original amino acid sequence as disclosed in the present invention in no more that 50%, more preferably not more than 35% and most preferably not more than 10%.

In a preferred embodiment of the present invention, the term derivative or fragment particularly refers to a peptide comprising an amino acid sequence selected from the group of SEQ ID NOs:87, 88, 89, 90, 91, 92, 93, 94, 95, 96, 97, 98, 99, 100, 101, 102, 103, 104, 105, 106, 107, 108, 109, 110, 111, 112, 113, 114, 114, 115, 116, 117, 118, 119, 120, 121, 122, 123, 124, 125, 126, 127, 128, 129, 130, 131, 132 (see TABLE 2).

More preferably, the peptide, a fragment or derivative thereof, of the present invention comprises an amino acid sequence selected from the group of SEQ ID NOs:90, 91, 98, 99, 111, 118, 123, 124, 127, 128, 132. These SEQ ID NOs directly resemble numbers 4, 5, 12, 13, 25, 32, 37, 38, 41, 42, 46 in TABLE 2 (or peptide numbers 5, 7, 15, 16, 40, 54, 65, 69, 75, 77, 90 according to the inventors' numbering system). Particularly preferred is a peptide comprising the SEQ ID NO: 127 (corresponds to No. 41 in TABLE 2, or, respectively, peptide number 75 according to the inventors numbering system)

In the context of the present invention, the term derivative or fragment of peptides further includes peptides which are shortened at their carboxyterminal end. The inventors have found that, for example, amino acids alanin, glutamic acid, isoleucin, tyrosin, glutamic acid, serin (A-E-I-Y-E-S) (SEQ ID NO: 133), which are the last six carboxyterminal amino acids of most peptides of SEQ ID NOs: 87-132, can be omitted, without losing the characteristic functional properties of the respective peptides. However, it is also possible that the peptides of the present invention are carboxyterminally shortened by more than these six amino acid, provided that the binding and functional properties of the peptides remain unaffected.

According to a preferred embodiment of the present invention, the peptide of the present invention, the fragment or derivative thereof is not:

(i) a peptide comprising $AX_1$, wherein $X_1$ is V, I, or L
(ii) a peptide comprising $AX_1X_2$, wherein $X_1$ is V, I, or L, preferably V, and $X_2$ is P or A, preferably P.
(iii) a tetrapeptide
(iv) a tetrapeptide having the sequence X1-X2-X3-X4, wherein X1 is A, X2 is V, T or I, X3 is P or A, and X4 is F, Y, I or V.

The peptides of the present invention bind to IAPs. Preferably they bind to human IAPs selected from the group consisting of c-IAP1, c-IAP2, XIAP, NAIP, survivin and livin/ML-IAP, and/or a fragment or derivative of any of the aforementioned IAPs. Livin/ML-IAP will be referred to as livin hereinafter. More preferably, the peptides bind to survivin and livin, and most preferably said peptides bind to livin.

It is important to note that the peptides of the present invention do not interact with livin via their amino terminal end, as it has been described in the art for other IAP-binding proteins like for example Smac/DIABLO. The amino terminal end of the peptides of the present invention is not freely accessible for any possible interaction with an IAP, since it is fused (for experimental purposes) to activation domain of the so-called GAL4 transcription activator (see EXAMPLES). Thus, it is obvious to the skilled artisan that the peptides of the present invention differ from those described in the art.

The peptides of the present invention can be identified by methods well known to the person skilled in the art. In general, the identification is achieved by contacting a peptide library with the desired interaction partner, e.g. livin, and selecting those which successfully bind. Among the known methods are screening of peptides libraries by e.g. phage display, ribosome display, mRNA display and yeast and/or mammalian two-hybrid systems. The preferred method to identify the peptides of the present invention is the two-hybrid approach. Particularly preferred is the use of the two-hybrid system to perform a so-called "peptide aptamer screening" (see EXAMPLES).

For peptide aptamer screening, the peptides of the library can optionally be anchored at both ends within a so-called scaffold protein, leading to a more preferred conformational stage of the peptides. Known scaffold proteins comprise e.g. *E. coli* thioredoxin A (trxA), staphylococcal nuclease, protease inhibitor eglin, Tendamistat from *Streptomyces tendea*, cellular transcription factor Sp1, and green fluorescent protein GFP. The preferred scaffold protein of the present invention is trxA.

Optionally, the peptides can be linked to a second moiety to create a so-called fusion protein. The fusion partner can be a carrier, which is preferably a protein, a fragment or derivative thereof, the attachment of which to any of the peptides, fragment or derivative thereof enables the penetration of the peptides through the cell membrane into the cell. Appropriate carriers, in particular proteins, are known to the person skilled in the art and include TAT, influenza virus hemagglutinin, the VP22 protein from herpes simplex virus, Antennapedia, fibroblast growth factor, Galparan (transportan), poly-arginine, Pep-1. Other carriers known to a person skilled in the art which do not belong to proteins, but mediate the internalization of molecules into cells include lipids and cationic lipids.

When a protein is used as a carrier, the term derivative or fragment of a protein refers to peptides in which one or more aminoacids can be substituted by other aminoacids different from the original one(s), or peptides the aminoacid sequence of which is either extended, shortened, or both, on either the aminoterminal, or the carboxyterminal or both ends, with respect to the original one(s), provided that the function as a carrier for the cellular uptake of the peptides remains unaffected. The above definition relates to TAT, influenza virus hemagglutinin, the VP22 protein from herpes simplex virus, Antennapedia, fibroblast growth factor, Galparan (transportan), poly-arginine and Pep-1.

In a preferred embodiment of the present invention, the carrier the peptide is fused to is poly-arginine, particularly R7, R9 or R11 (peptides with 7, 9 or 11 arginine residues).

The linkage of the peptides to the carrier can occur by any chemical interaction known to the person skilled in the art, like chemical adsorption, dipole-dipole or the like. Preferably, the carrier is linked to the peptides by a chemical bond, in particular a covalent bond, in case the carrier is a protein. This bond must be such that it remains unaffected before and while penetrating the cell membrane and, if necessary for the interaction of the peptides with IAPs, can be cleaved. In general, the peptide/carrier entity can interact with IAPs to the necessary extent, a cleavage being not necessary.

It is also possible that the carrier, also known to the skilled artisan as protein transduction domain (PTD), is linked to the peptide of the present invention via disulfide bonds instead of covalent linkage. This bears the advantage, that the reducing milieu within a cell leads to the cleavage of the linked PTD, and, thus, potential negative side effects of the PTD on the function of the peptide of the present invention can be avoided.

A further embodiment of the present invention relates to a nucleic acid, preferably a DNA, coding for a peptide of the present invention. The nucleic acids coding for the peptides of the present invention can be placed in expression vectors capable of expressing an encoded protein, polypeptide or peptide. Nucleic acids are inserted into vectors from which they may be expressed by methods known to the person skilled in the art. Vectors may, if desired, contain nucleic acids encoding portions of other proteins, thereby providing a fusion protein.

Therefore, the present invention is also directed to a recombinant DNA and an expression vector which includes any one of the present nucleic acids operably linked to regulatory control nucleic acid which effects expression of the nucleic acid in a host cell. The present invention is further directed to a host cell which contains such a recombinant DNA or such an expression vector.

Expression vectors include plasmids designed for the expression of proteins or polypeptides fused to or within bacterial phage coat proteins. The DNA encoding the desired peptide, whether in a fusion, premature or mature form, may be ligated into expression vectors suitable for any host. The DNA encoding the desired polypeptide may also contain a signal sequence to permit secretion from the intended host. Both prokaryotic and eukaryotic host systems are contemplated.

The present invention also contemplates a process for producing a recombinant peptide or immunogenic fragments thereof, encoded by a nucleic acid of the present invention. The process involves: a) culturing a host cell which contains an expression vector having one of the nucleic acids of the present invention in a culture medium under conditions suitable for expression of one of said recombinant proteins in the host cell, and b) isolating the recombinant protein from the host cell or the culture medium.

The peptides of the present invention, whether in a premature, mature or fused form, are isolated from lysed cells, or from the culture medium, and are purified to the extent needed for the intended use. One of skill in the art can readily purify these proteins, polypeptides and peptides by any available procedure. For example, purification may be accomplished by salt fractionation, size exclusion chromatography, ion exchange chromatography, reverse phase chromatography, affinity chromatography and the like.

The present invention further contemplates antibodies which can bind to the present peptides or fusion peptides, derivatives and fragments thereof. Such antibodies preferably bind to unique antigenic regions or epitopes in the peptides of the present invention. The antibody can be monoclonal or polyclonal. To generate an antibody, animals, preferably rabbits, chicken or mice are immunized with at least one peptide of the present invention, or a fragment or derivative thereof. The raised antibodies can be isolated by well-known methods.

Epitopes and antigenic regions useful for generating antibodies can be found within the present peptides by procedures available to one of skill in the art. For example, short, unique peptide sequences can be identified in the present proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the present proteins and polypeptides. These surface epitopes are more readily detected in samples tested for the presence of the present proteins and polypeptides.

Peptides for immunization can be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art can use available procedures and coupling reagents to link the desired peptide epitope to such a carrier. For example, coupling reagents can be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies can vary widely. The minimum size must be sufficient to provide an antigenic epitope which is specific to the peptide. The maximum size is not critical unless it is desired to obtain antibodies to one particular epitope. For example, a large polypeptide may comprise multiple epitopes, one epitope being particularly useful and a second epitope being immunodominant.

The peptides of the present invention and/or their coding nucleic acids are particularly useful to sensitize cells, particularly tumor cells, which are resistant to various treatment strategies to apoptosis. Whether the cells have been rendered to undergo apoptosis upon application of a peptide or a nucleic acid of the present invention can be determined by a variety of methods known to the person skilled in the art, like for example TUNEL assay (Terminal Deoxynuceotidyltransferase-mediated UTP End Labelling), determination of PARP cleavage by immunological methods, so-called caspase assays etc.

Furthermore, the peptides of the present invention and/or their coding nucleic acids, can be used as a pharmaceutical, optionally in combination with at least one active compound. This is a further embodiment of the present invention. The term "active compound" refers to a compound other than the peptide, a fragment or derivative thereof, which is able to induce apoptosis or which inhibits cell proliferation.

Active compounds which are able to induce apoptosis are known to the person skilled in the art. One class of active compounds are chemical compounds having a cytostatic or antineoplastic effect ("cytostatic compound"). Cytostatic compounds included in the present invention comprise, but are not restricted to (i) antimetabolites; (ii) DNA-fragmenting agents; (iii) DNA-crosslinking agents; (iv) intercalating agents; (v) protein synthesis inhibitors; (vi) topoisomerase I poisons; (vii) topoisomerase II poisons; (viii) microtubule-directed agents; (ix) kinase inhibitors; (x) miscellaneous investigational agents; (xi) hormones and (xii) hormone antagonists.

More specifically, the class of active compounds having a cytostatic or anti-neoplastic effect ("cytostatic compound") as indicated above included in the present invention comprise, but are not restricted to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphteria toxin; (vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists.

In a preferred embodiment of the present invention the cytostatic compound is selected from the group consisting of cisplatin, doxorubicin and mitomycin C. Most preferred, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor α (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. Preferably, the death receptor ligand is TNF-α.

Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti TNF-R1 antibody and anti-TRAMP (DR3) antibody as well as fragments and derivatives of any of said antibodies.

For the purpose of sensitizing cells for apoptosis, the peptides and the nucleic acids of the present invention can be also used in combination with radiation therapy.

The phrase "radiation therapy" refers to the use of electromagnetic or particulate radiation in the treatment of neoplasia. Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles and Practice of Oncology, 24875 (Devita et al., 4$^{th}$ ed., v1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme; they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

Generally, radiation therapy can be combined temporally with other active compounds listed above to improve the outcome of treatment. There are various terms to describe the temporal relationship of administering radiation therapy together with other active compounds, and the following examples are the preferred treatment regimens and are generally known by those skilled in the art and are provided for illustration only and are not intended to limit the use of other combinations. Administration of radiation therapy with other active compounds can be "sequential", i.e. separately in time in order to allow the separate administration, "concomitant" which refers to the administration on the same day, and, finally, "alternating" which refers to the administration of radiation therapy on the days in which other active compounds would not have been administered.

A further object of the present invention are pharmaceutical preparations which comprise an effective dose of at least one of the disclosed peptides and/or one of their coding nucleic acids, and/or at least one active compound and a pharmaceutically acceptable carrier, i.e. one or more pharmaceutically acceptable carrier substances and/or additives.

The dosage of the polypeptide or the nucleic acid, in combination with one or more active compounds to be administered, depends on the individual case and is, as is customary, to be adapted to the individual circumstances to achieve an optimum effect.

The peptides and their coding nucleic acids according to the present invention, respectively the medicaments containing the latter, can be used for the treatment of all cancer types which fail to undergo apoptosis. Examples of such cancer types comprise neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeolid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma.

In a preferred embodiment of the invention, the cancer to be analyzed, diagnosed and treated is melanoma.

A further embodiment of the present invention is a diagnostic kit comprising at least one peptide of the present invention, and/or a nucleic acid encoding a peptide, a vector and a host cells.

The diagnostic kit can be used to detect IAPs, particularly livin, in tumor cells that fail to undergo apoptosis, in particular melanoma. Methods to determine the presence and amount of IAPs in a given sample are well known to the person skilled in the art. Briefly, a sample is provided, said sample is contacted with a peptide that specifically binds to livin and the presence or amount of the peptide bound to livin is determined, whereby the presence or amount of livin in said sample is determined. Methods to determine the amount and presence of peptides comprise, among others, Western blotting, immunoprecipitation, ELISA, and RIA. For these purposes the peptides and nucleic acids of the present invention can be labelled with a suitable marker well-known to the person skilled in the art.

Peptides of a peptide expression library with a length of 20 amino acids are co-expressed as a fusion peptides fused to a transcriptional transactivator domain (GAL4AD), together with the target protein X (e.g. livin) which is fused to a DNA binding domain (GAL4BD). Upon successful binding of a peptide with the target protein, a synthetic transcription factor is created which in turn binds to the binding site and activates the transcription of a selection marker (e.g. ADE2). Using selective growth conditions, e.g. lacking adenine on growth media, only those yeast colonies are able to grow, which express a peptide that binds to the target (NLS: nuclear localization signal; TAG: suitable marker to detect the peptide aptamer; trxA: *E. coli* Thioredoxin A scaffold)

Figure 1:
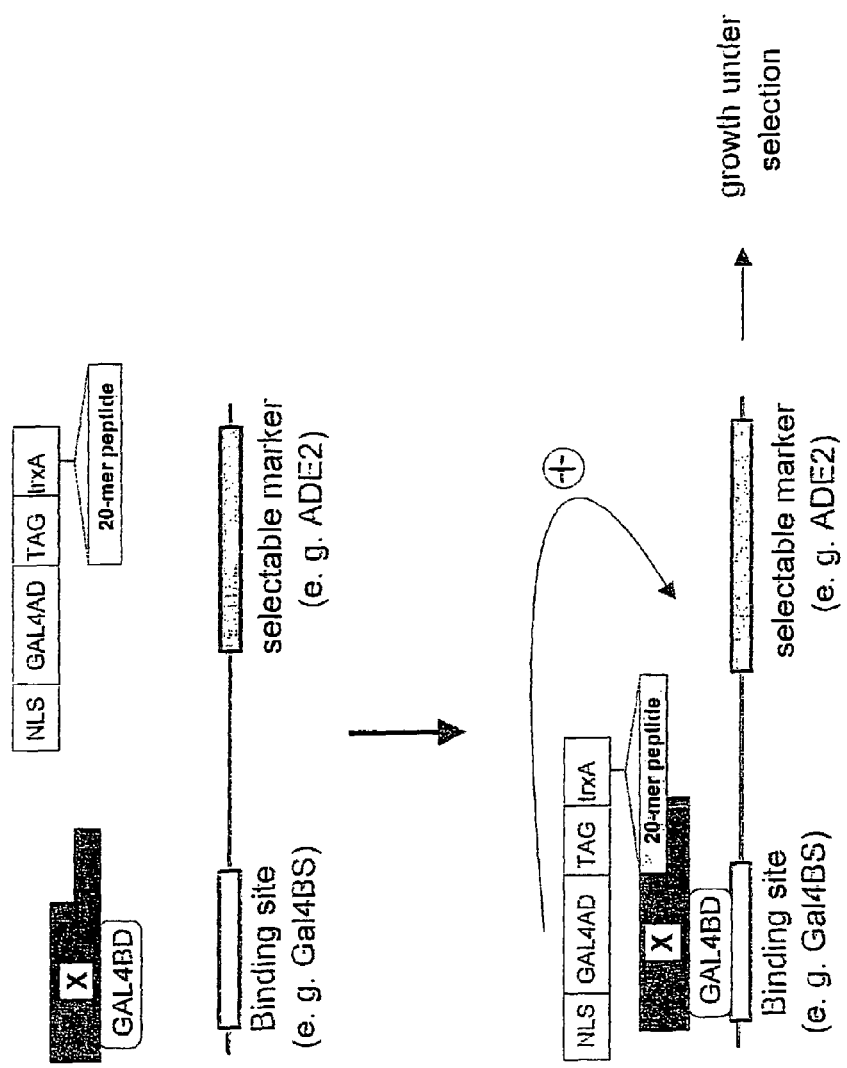
FIG. 1: Modified "Peptide Aptamer System" in *S. cerevisiae*.
Figure 2:
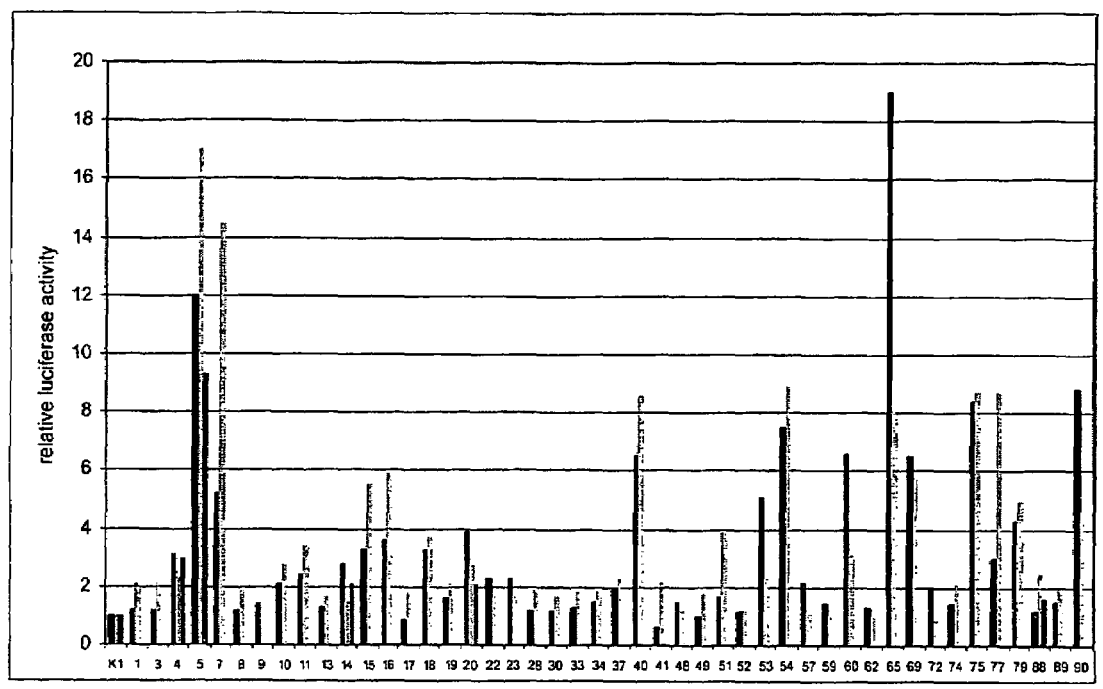

FIG. 2: Interaction in mammalian cells

The FIG. 2 shows the interaction results from a mammalian Two-Hybrid-System (CheckMate, Promega, Madison Wis.). The Y-axis displays relative luciferase activity of the peptides of the present invention (particularly SEQ ID NOs: 87-132). The differently stained bars represent independent Check-Mate analyses.

Figure 3:
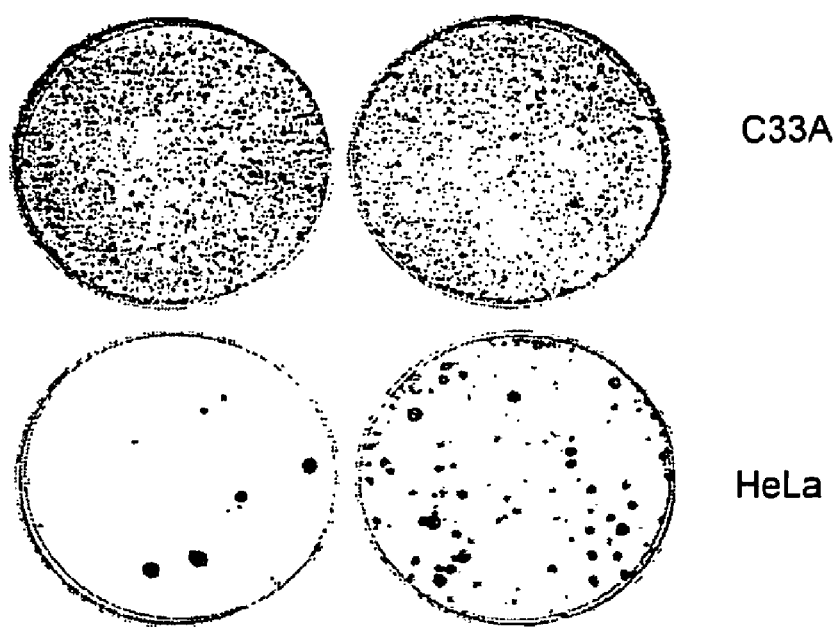

FIG. 3: Colony formation assay

Expression vectors bearing the nucleic acid coding for peptide number 75 (corresponds to SEQ ID No: 127 or number 41 of TABLE 2) or bearing the nucleic acid coding for control peptide were introduced in HeLa cells and livin-negative C33a cells. The cells were selected for stable transfectants.

Figure 4:
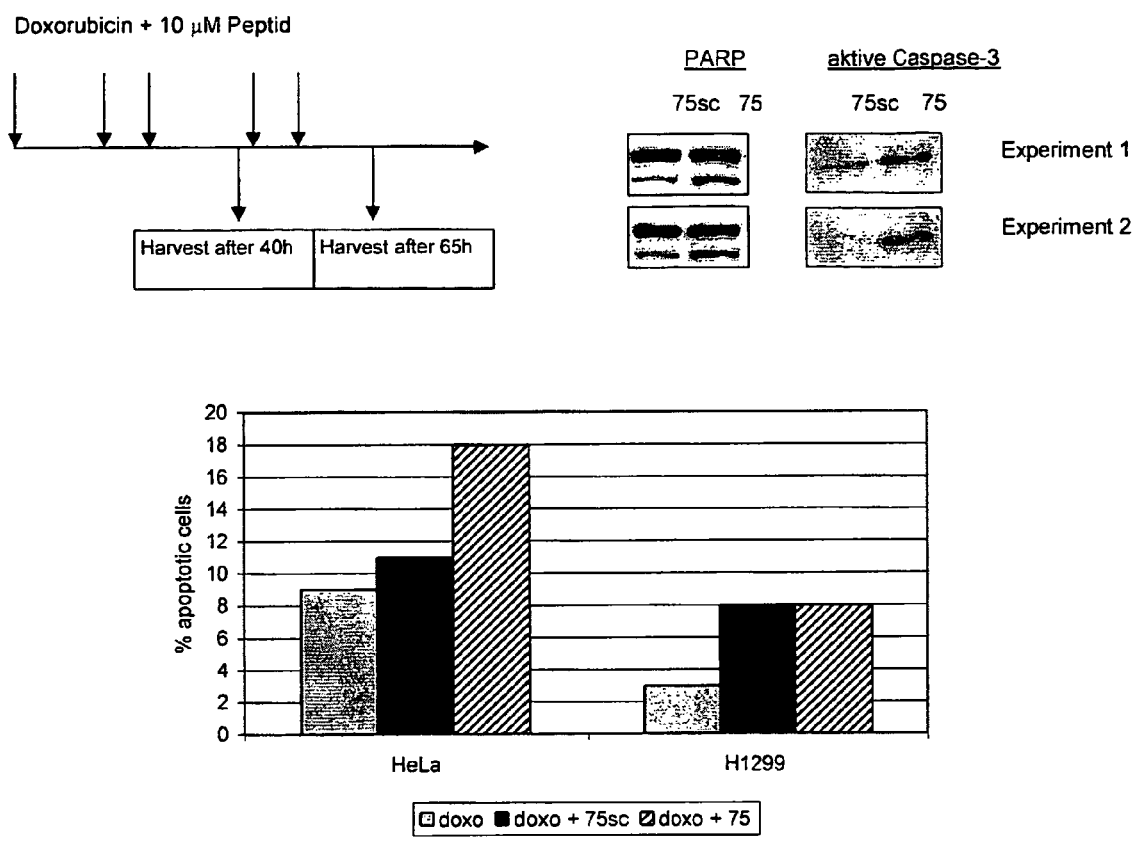

FIG. 4: Induction of apoptosis

Peptide number 75 as defined for FIG. 3, linked to poly-arginine R9, was added to the cell culture medium of HeLa cells and livin-negative H1299 cells. Upper panel left of FIG. 4 shows the scheme of how cells were treated with the cytostatic compound doxorubicin (0.5 µg/1 ml). Upper panel right shows Western Blot of active caspase 3 and cleaved PARP. Lower panel shows increase of apoptotic cells.

TABLE 1: Sequences of Peptides

The Table displays the sequences of the 86 peptides of the present invention (NS=nucleotide sequence; AS=amino acid sequence; *=break of peptide chain, resulting in a "linear peptide" fused to the N-terminal part of trxA; ND=Not Determined))

TABLE 2: Sequences of Linear Peptides

Table 2 lists so-called linear peptides being not embedded in a thioredoxin A scaffold as it is commonly done for aptamers (SEQ ID NOS 87-132, respectively, in order or appearance). Linear peptide banks are generated by expressing randomized 20-mer peptides during a screening procedure as GAL4AD fusions (i.e. aminoterminally fused to the GAL4activation domain). This results in peptides with a free carboxyterminal end.

TABLE 3: Specificity for Livin

Table 3 lists the peptides with high specificity to livin versus other IAPs. The numbers of the peptides in the first column reflects the inventors' numbering (5=SEQ ID:90, 7=SEQ ID:91, 15=SEQ ID:98, 16=SEQ ID:99, 40=SEQ ID:111, 54=SEQ ID: 18, 65=SEQ ID123, 69=SEQ ID:124, 75=SEQ ID 127, 77=SEQ ID:128, 90=SEQ ID:132). K1 refers to a control peptide. Livin-β, c-IAP-1, c-LAP-2, XIAP and survivin refer to different IAPs being tested for binding. HPV16 E6 refers to human papilloma virus type 16 E6 protein being used as a control.

EXAMPLES

Example 1

Screening for Livin-Binding Peptides

A method derived from the "peptide aptamer system" is used. Yeast strain KF1 (MATa trp1-901 leu2-3,112 his 3-200 gal4Δ gal80Δ LYS2::GAL1-HIS3 GAL2-ADE2 met2::GAL7-lacZ SPAL10-URA3) is generated from PJ69-4A after integration at the ura3-52 locus by homologous recombination of PCR product encompassing the SPAL10-URA3 allele from yeast strain MaV103. KF1 thus contains three selectable marker genes under the control of Gal4-binding sites: GAL2-ADE2, GAL1-HIS3 and SPO13-URA3. As bait, the complete livin sequence is fused in frame to the Gal4 DNA-binding domain into vector pPC97, yielding pPC97/livin. A yeast expression vector, pADtrx, in which the ADH1 promoter directs the expression the E. coli thioredoxin A (trxA) fused to the Gal4 activation domain, is constructed from pRS424. In addition, pADtrx contains the simian virus 40 nuclear localization signal and an influenza hemagglutinin epitope. A randomized peptide expression library is generated in pADtrx by cloning randomized 60-mer oligonucleotides into the unique RsrII site of trxA. Oligonucleotides contained triplets of the sequence NKK (where N=G, A, T or C and K=G or C), which encode for all 20 amino acids but result in only one stop codon. The complexity of the peptide aptamer expression library is estimated to be in the range of $2 \times 10^8$ different members.

KF1 transformants expressing pPC97/livin and the peptide aptamer expression library are selected initially for growth in the absence of adenine. Subsequently, they are analyzed by replica plating for activation of the Gal4-dependent GAL2-ADE2, GAL1-HIS3 and SPO13-URA3 genes. Peptide aptamer expression vectors from clones exhibiting growth in the absence of adenine and histidine are rescued, and activation of the selectable markers is verified by rescreening. Binding specificity of livin binding aptamers was tested by using control proteins as baits like HPV16 E6 or HPV16E7.

Using the above method, 38 peptides have been identified that in the context of trxA specifically interact with livin (see Table 1 SEQ ID NOS: 1-38). Alternatively, a peptide aptamer library was directly fused to the Gal4 activation domain, giving rise to "linear" peptides that are not embedded in the trxA scaffold. Using this approach, another 48 peptides that specifically interact with livin have been identified (Table 1 SEQ ID NOS:39-86).

Peptides according to SEQ ID NOs:87-132 are also so-called "linear" peptides, not being embedded in a TrxA scaffold.

Example 2

Mammalian Two-Hybrid Analyses

In order to analyze the aptamer/livin interactions in human cells, the "CheckMate™ Mammalian Two-Hybrid System" (Promega GmbH, Mannheim, Germany) is employed. The complete livin protein was expressed as a Gal4 binding domain fusion protein from pBIND. Individual peptide aptamers are expressed within the trxA scaffold, linked to the transcriptional activation domain of the herpes simplex virus-1 VP16 protein, from pACT. Reporter plasmid pG51uc contains the firefly luciferase under the transcriptional control of five Gal14-binding sites. Cells are harvested 24 hours after transfection, and luciferase activities are measured by methods known to the person skilled in the art.

Using this approach, it is shown that the interaction of the selected peptides to livin occurs also in mammalian cells.

As shown in FIG. 2, the majority of linear petides according to TABLE 2 (SEQ ID NOs: 87-132), interact in mammalian cells with livin, as verified by a high luciferase activity.

Example 3

Specificity for Livin

For further analyses in the yeast two hybrid system, i.e. the interaction with other IAPs that livin, 11 peptides (see TABLE 3) which exerted the highest activity in the mammalian Two-Hybrid-System were chosen. As depicted in Table 3, the peptides of the present invention bind in a highly specific manner to Livin (beta) and not or only to a neglectible extent to other IAPs. This is particularly advantageous for the use of the peptides for therapeutic purposes, since livin is highly expressed only in tumor cells. Other IAPs may fulfil physiologic functions in non-tumorous cells. Thus, a binding and inactivation of these IAPs can result in undesired side effects.

Example 4

Livin-Binding Peptides Block Growth of Livin-Binding HeLa Cells

The nucleic acids coding for the peptides of TABLE 3 were cloned into mammalian expression vectors and transfected into different cells to observe their further growth. By using a HIS-tag it was possible to verify that all peptide sequences could be expressed. As depicted in FIG. 3, most of the peptides, in particular peptide number 75, blocked the growth of livin-expressing HeLa and MeWo (melanoma cells), whereas livin-negative cells like C33a were not affected.

Example 5

Livin-Binding Peptide Fused to a Carrier Sensitizes Livin-Positive Cells for Apoptosis A synthetic peptide by fusing peptide number 75 (SEQ ID NO:127) to poly-arginine R9 was generated by methods known to the person skilled in the art. After adding the fusion peptide to the culture medium, an efficient intracellular uptake of the peptide could be verified by using a HIS-tag (100% of cells within 20 min). The ectopic expression of the peptide leaded to a sensitization of livin-positive cells for pro-apoptotic drugs, e.g. cytostatic compounds like doxorubicin). The repeated addition of doxorubicin resulted in a increased concentration of active caspase as shown in FIG. 4. The control peptide sc75 (scrambled form of peptide number 75 with randomised amino acid sequence) did not have this effect. The increased caspase-3 activity directly correlated with an increased cleavage of the caspase-3 substrate PARP and an increase of apoptosis of HeLa but not of H1299 cells.

TABLE 1

SEQUENCE IDENTIFICATION NUMBERS

| SEQ ID NO | NAME | NS | AS | Sequence |
|---|---|---|---|---|
| 1 | LT 1-1 | 60 | 20 | WLGTFSGTCSTAFYFPLGVP |
| 2 | LT 6-1 | 60 | 20 | CRWLRTKRTLPLFSVMPFWC |
| 3 | LT 7-1 | 61 | 31 | MYSNVSVDVAADGVSCVCCSWSVQNDRPDSG* |
| 4 | LT 8-2 | 60 | 20 | YKWRMGVYLSGVRLMRAFII |
| 5 | LT 9-1 | 60 | 20 | VSYRTCTAGGQMSRWRLFII |
| 6 | LT 12-1 | 60 | 20 | GYSLTSMSAFAVRPCVCGSL |
| 7 | LT 13-1 | 60 | 20 | WLGTFSGTCSTAFYFPLGVP |
| 8 | LT 15-2 | 60 | 20 | TNFRPSPTFHAILLWPNTFS |
| 9 | LT 16-1 | 60 | 20 | VGLGGWCFDCYWVAWDFQTQ |
| 10 | LT 19-2 | 60 | 20 | FWDYCGPLICLHCNLGRCVS |
| 11 | LT 21-2 | 61 | 5 | MMDSA* |
| 12 | LT 22-2 | 60 | 20 | ASLRLYPIGGTVPFGRTGAG |
| 13 | LT 23-2 | 60 | 20 | GDYGCCWVVTTGVGVRCYVW |
| 14 | LT 27-1 | 60 | 20 | ACWALWSLFRQDLLLVITFD |
| 15 | LT 28-1 | 61 | 31 | DSAPGERYFVDFLGVSFACVWSVQNDRPDSG* |
| 16 | LT 29-1 | 60 | 14 | IPWAPPMYFADSNV* |
| 17 | LT 33-1 | 60 | 20 | TPSCRAGVLRCTGCFGVRSG |
| 18 | LT 34-2 | 60 | 20 | LWRGRTVSAYLSWLRHYSSS |
| 19 | LT 35-1 | 60 | 20 | HSRPALCMVSLRWARSLWIV |
| 20 | LT 37-2 | 42 | 14+? | WTHVWVGWLVAGMS |
| 21 | LT 38-1 | 60 | 20 | RFRCRADLCVTLTVLSFLAQ |
| 22 | LT 45-2 | 60 | 20 | CLETLRVCPYVARIAIQHLR |
| 23 | LT 48-3 | 60 | 20 | LLAWRVQQSRPLPYLHIAFI |
| 24 | LT 49-2 | 60 | 20 | PPPLTGRWSRQCVSVFGIVH |
| 25 | LT 54-1 | 60 | 20 | CWIHRAWMLSWHGVWSLTLV |

TABLE 1-continued

SEQUENCE IDENTIFICATION NUMBERS

| SEQ ID NO | NAME | NS | AS | Sequence |
|---|---|---|---|---|
| 26 | LT 62-1 | 60 | 20 | APPISGRWRGLYMRSRFVSL |
| 27 | LT 76-3 | 60 | 18 | VRLFIVCIIICCLMLLVG* |
| 28 | LT 79-1 | 60 | 20 | IPSCSVLVCLCHLARLWHCE |
| 29 | LT 82-3 | 60 | 20 | CSVMHVFRVGPGSSGSLSCG |
| 30 | LT 93-1 | 126 | 42 | RATYWFRSRYQVVHRSRLPYGPLIVVGIGALNLELNRTLLCS |
| 31 | LT 103-1 | 60 | 20 | SLAIWSTQSCARCQCTLSRV |
| 32 | LT 105-2 | 60 | 20 | FWFLPAPPCKCGLLYRLSVH |
| 33 | LT 108-1 | 60 | 20 | LAGRHFSRVVDRIRYRLLWT |
| 34 | LT 126-2 | 60 | 20 | MPIPPLCRSAGRLLYLYTHY |
| 35 | LT 127-1 | 60 | 20 | YTLPSVLLCLMRTGMLRCAC |
| 36 | LT 135-2 | 60 | 20 | GMPIRASPCYLGVDGWCXTL |
| 37 | LT 138-2 | 60 | 20 | KPWEYLRMFPWMRVARFFIW |
| 38 | LT 140-2 | 60 | 20 | ALLMFGCPNWFASWRLHLFI |
| 39 | ND | ND | ND | EFGSGLVSGRGIIVRRMLFLRVLLWVLRSAEIYES* |
| 40 | ND | ND | ND | GPFENWRVEELARGRYRMHGDVVLRSAEIYES* |
| 41 | ND | ND | ND | GPIDCIIFLLWYSRQQRGGSRGGP* |
| 42 | ND | ND | ND | GSRFRVFVCSLFSFLSGRGGGVVVLRSAEIYES* |
| 43 | ND | ND | ND | GPFKRCHERLVAFARCWFMWSMVLRSAEIYES* |
| 44 | ND | ND | ND | GPSNDNQLVLRVRILRVLIVMRVLRSAEIYES* |
| 45 | ND | ND | ND | EFRVRRMRLLVRLMGSDDSGTIPDFGP* |
| 46 | ND | ND | ND | GPSLQFLEVVVSCYMVLYDLSKGP* |
| 47 | ND | ND | ND | GPQPFCSPPSFYTRLLIIVRLLSLDLQRSSNRRY* |
| 48 | ND | ND | ND | GPAPLSLCVCKCGCGHTRPFVGP* |
| 49 | ND | ND | ND | GPDVHIWQSIIFYAMRHMMGP* |
| 50 | ND | ND | ND | EFGSGCGCFVRGRIVRIRCVILLLRVLRSAEIYES* |
| 51 | ND | ND | ND | GPHSSAHDRIWLRVRGLRIILLVLRSAEIYES* |
| 52 | ND | ND | ND | EFGSGLCVRRWWGMSVGSRIMLVMLVLRSAEIYES* |
| 53 | ND | ND | ND | GPVYSEAFVCLVCAGVCVEECGGSLDLQRSSNRRY* |
| 54 | ND | ND | ND | GPIETVGFIVRLHTLLMVLRRTGP* |
| 55 | ND | ND | ND | GPLHRTLLVDMCCWLMSLESNMGP* |
| 56 | ND | ND | ND | EFGVRVVCVVRSLFVLRCGLLRCRGVLRSAEIYES* |
| 57 | ND | ND | ND | EFVRECSLCRVMVLMFVLRGIRLRVLRSAEIYES* |
| 58 | ND | ND | ND | EFGVRLLVLLRLRCVRRGGGCFVCWVLRSAEIYES* |
| 59 | ND | ND | ND | GSGFRMRVLVMVCRLRVVFLVRRVLRSAEIYES* |
| 60 | ND | ND | ND | GRLGWLRLLCVRIVLVCLRRGLVLRSAEIYES* |
| 61 | ND | ND | ND | EFGSGWYVDLGDYSVWVDYVYCGSGSLDLQRSSNRRY* |
| 62 | ND | ND | ND | GPSQCAQRVALIQMYIDALVCIGP* |

TABLE 1-continued

SEQUENCE IDENTIFICATION NUMBERS

| SEQ ID NO | NAME | NS | AS | Sequence |
|---|---|---|---|---|
| 63 | ND | ND | ND | EFGSGCVRIRVGIVRRMLXLRFVFLVLRSAEIYES* |
| 64 | ND | ND | ND | GPLLDPMLRQRFSLRVWIMLLGVLRSAEIYES* |
| 65 | ND | ND | ND | GPNSWVWRYVTIAHWLANYRMSGP* |
| 66 | ND | ND | ND | GPAMKSCTIRVFRVCIVLRIVRVLRSAEIYES* |
| 67 | ND | ND | ND | EFGVRMRLMIRIFRGLFVLRGFRGLVLRSAEIYES* |
| 68 | ND | ND | ND | GPVPSSPCSFLLYCRDVLCHWPGP* |
| 69 | ND | ND | ND | GPCEPFIGDCWPCLIRTLVTLRGLDL |
| 70 | ND | ND | ND | GPWWKDRGVLVRLCVLRLVVGVVLRSAEIYES* |
| 71 | ND | ND | ND | GPRLLVRMRGWCRVSLIXFWLRVLRSAEIYES* |
| 72 | ND | ND | ND | EFRVRIIVVSLRIWRLLVRRCLCLVLRSAEIYES* |
| 73 | ND | ND | ND | GPVECADVLFASRIRLLCLCFRVLRSAEIYES* |
| 74 | ND | ND | ND | EFGRRLLVFRLSVFVVVLGRRLSRVLRSAEIYES* |
| 75 | ND | ND | ND | GAGLGRVIRLRIVVLRCIFLLFRVLRSAEIYES* |
| 76 | ND | ND | ND | GPFPFDYPRWIMIVLLRGVLRSAEIYES* |
| 77 | ND | ND | ND | GSRGLRLCLLGRCRLCGCLIIMRVLRSAEIYES* |
| 78 | ND | ND | ND | GPESYVLWPARGEALYYLRAWLGP* |
| 79 | ND | ND | ND | GSRCIRRRISILFFVFRVLRSRRVLRSAEIYES* |
| 80 | ND | ND | ND | GPFSEHARGHVVTICRLRLLFWLLRSAEIYES* |
| 81 | ND | ND | ND | GPSSLLRRCLILGMVLGVLRRRVLRSAEIYES* |
| 82 | ND | ND | ND | GPHPVLAVQLINAYLGLERVGRGP* |
| 83 | ND | ND | ND | GPLPSGAVSTEAYFWEVFKLLMGP* |
| 84 | ND | ND | ND | GPYPYLRILLVQKIACVRRALWVLRSAEIYES* |
| 85 | ND | ND | ND | GPVGVEGVDSVFGWCVVCFLLVWSLDLQRSSNRRY* |
| 86 | ND | ND | ND | EFRVRVLGCMGVFLRLRFCGGLRLRVLRSAEIYES* |

TABLE 2

| Number | Peptide | Sequence |
|---|---|---|
| 1 | 1 | GSGLVSGRGIIVRRMLFLRVLLWVLRSAEIYES* |
| 2 | 3 | GPFENWRVEELARGRYRMHGDVVLRSAEIYES* |
| 3 | 4 | GPIDCIIFLLWYSRQQRGGSRGGP* |
| 4 | 5 | GSRFRVFVCSLFSFLSGRGGGVVVLRSAEIYES* |
| 5 | 7 | GPFKRCHERLVAFARCWFMWSMVLRSAEIYES* |
| 6 | 8 | GPSNDNQLVLRVRILRVLIVMRVLRSAEIYES* |
| 7 | 9 | RVRRMRLLVRLMGSDDSGTIPDFGP* |
| 8 | 10 | GPSLQFLEVVVSCYMVLYDLSKGP* |
| 9 | 11 | GPQPFCSPPSFYTRLLIIVRLLSLDLQRSSNRRY* |
| 10 | 13 | GPAPLSLCVCKCGCGHTRPFVGP* |
| 11 | 14 | GPDVHIWQSIIFYAMRHMMGP* |
| 12 | 15 | GSGCGCFVRGRIVRIRCVILLLRVLRSAEIYES* |
| 13 | 16 | GPHSSAHDRIWLRVRGLRIILLVLRSAEIYES* |
| 14 | 17 | GSGLCVRRWWGMSVGSRIMLVMLVLRSAEIYES* |
| 15 | 18 | GPVYSEAFVCLVCAGVCVEECGGSLDLQRSSNRRY* |
| 16 | 19 | GPIETVGFIVRLHTLLMVLRRTGP* |
| 17 | 20 | GPLHRTLLVDMCCWLMSLESNMGP* |
| 18 | 22 | GVRVVCVVRSLFVLRCGLLRCRGVLRSAEIYES* |
| 19 | 23 | VRECSLCRVMVLMFVLRGIRLRVLRSAEIYES* |

TABLE 2-continued

| Number | Peptide | Sequence |
|---|---|---|
| 20 | 28 | GVRLLVLLRLCVRRGGGCFVCWVLRSAEIYES* |
| 21 | 30 | GSGFRMRVLVMVCRLRVVFLVRRVLRSAEIYES* |
| 22 | 33 | GRLGWLRLLCVRIVLVCLRRGLVLRSAEIYES* |
| 23 | 34 | GSGWYVDLGDYSVWVDYVYCGSGSLDLQRSSNRRY* |
| 24 | 37 | GPSQCAQRVALIQMYIDALVCIGP* |
| 25 | 40 | GSGCVRIRVGIVRRMLFLRFVFLVP* |
| 26 | 41 | GPLLDPMLRQRFSLRVWIMLLGVLRSAEIYES* |
| 27 | 48 | GPNSWVWRYVTIAHWLANYRMSGP* |
| 28 | 49 | GPAMKSCTIRVFRVCIVLRIVRVLRSAEIYES* |
| 29 | 51 | GVRMRLMIRIFRGLFVLRGFRGLVLRSAEIYES* |
| 30 | 52 | GPVPSSPCSFLLYCRDVLCHWPGP* |
| 31 | 53 | GPCEPFIGDCWPCLIRTLVTLRGLDLQRSSNRRY* |
| 32 | 54 | GPWWKDRGVLVRLCVLRLVVGVVLRSAEIYES* |
| 33 | 57 | GPRLLVRMRGWCRVSLIXFWLRVLRSAEIYES* |
| 34 | 59 | RVRIIVSLRIWRLLVRRRCLCLVLRSAEIYES* |
| 35 | 60 | GPVECADVLFASRIRLLCLCFRVLRSAEIYES* |
| 36 | 62 | GRRLLVFRLSVFVVVLGRRLSRVLRSAEIYES* |
| 37 | 65 | GAGLGRVIRLRIVVLRCIFLLFRVLRSAEIYES* |
| 38 | 69 | GPFPFDYPRWIMIVLLRGVLRSAEIYES* |
| 39 | 72 | GSRGLRLCLLGRCRLCGCLIIMRVLRSAEIYES* |
| 40 | 74 | GPESYVLWPARGEALYYLRAWLGP* |
| 41 | 75 | GSRCIRRRISILFFVFRVLRSRRVLRSAEIYES* |
| 42 | 77 | GPFSEHARGHVVTICRLRLLFWLLRSAEIYES* |
| 43 | 79 | GPSSLLRRCLILGMVLGVLRRRVLRSAEIYES* |
| 44 | 88 | GPHPVLAVQLINAYLGLERVGRGP* |
| 45 | 89 | GPLPSGAVSTEAYFWEVFKLLMGP* |
| 46 | 90 | GPYPYLRILLVQKIACVRRALWVLRSAEIYES* |

TABLE 3

| (linear) peptide | Livinβ | c-IAP-1 | c-IAP-2 | XIAP | Survivin | HPV16 E6 |
|---|---|---|---|---|---|---|
| 5 | + | − | − | − | − | − |
| 7 | + | − | − | − | − | − |
| 15 | + | − | − | − | − | − |
| 16 | + | − | − | − | − | − |
| 40 | + | − | − | − | − | − |
| 54 | + | − | − | − | − | − |
| 65 | + | − | − | − | − | − |
| 69 | + | − | − | − | − | − |
| 75 | + | − | − | − | − | − |
| 77 | + | − | − | + | − | − |
| 90 | + | − | − | − | − | − |
| K1 | − | − | − | − | − | − |

The invention claimed is:

1. An isolated peptide which sensitizes cells for apoptosis comprising:
   (a) the amino acid sequence of SEQ ID NO: 127.

2. A composition comprising the peptide of claim 1 linked to a carrier which mediates the uptake of the peptide into a cell.

3. A method of sensitizing a livin-β-expressing cell for apoptosis, comprising administering to a livin-β-expressing cell the peptide of claim 1, optionally in combination with an intercalating agent, wherein said peptide binds to livin-β in said cell, and wherein said binding of peptide to livin-β sensitizes said cell for apoptosis.

4. The method of claim 3, wherein said cell is a cancer cell.

5. The method of claim 4, wherein said cancer cell is a melanoma cell.

6. A diagnostic kit for the detection of livin-β in cancer cells, comprising the peptide of claim 1 and a buffer.

* * * * *

UNITED STATES PATENT AND TRADEMARK OFFICE
CERTIFICATE OF CORRECTION

PATENT NO. : 7,544,768 B2  
APPLICATION NO. : 10/519539  
DATED : June 9, 2009  
INVENTOR(S) : Karin Hoppe-Seyler et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (80) days Delete the phrase "by 80 days" and insert -- by 0 days --

Signed and Sealed this

Twenty-fourth Day of November, 2009

David J. Kappos  
*Director of the United States Patent and Trademark Office*